United States Patent [19]

Aiba et al.

[11] Patent Number: 5,118,625
[45] Date of Patent: Jun. 2, 1992

[54] AUTONOMOUSLY REPLICATING PLASMID AND SACCHAROMYCOPSIS LIPOLYTICA TRANSFORMED THEREWITH

[75] Inventors: Shuichi Aiba, Saitama; Tomohisa Nagasaki, Tokyo; Kohji Uchida, Shiga, all of Japan

[73] Assignees: Oriental Yeast Co., Ltd.; Nisshin Flour Milling Co., Ltd., both of Tokyo, Japan

[21] Appl. No.: 285,032

[22] Filed: Dec. 16, 1988

[30] Foreign Application Priority Data

Dec. 17, 1987 [JP] Japan .................. 62-317320

[51] Int. Cl.⁵ .................. C12N 1/19; C12N 15/81
[52] U.S. Cl. .................. 435/255; 435/320.1
[58] Field of Search .................. 435/172.1, 252.3, 255, 435/256, 320, 940; 935/1, 9, 6, 16, 19, 23, 28, 33, 34, 37, 69, 111

[56] References Cited

FOREIGN PATENT DOCUMENTS 138508 10/1984 European Pat. Off.
166659 6/1985 European Pat. Off.
220864 10/1986 European Pat. Off.

OTHER PUBLICATIONS

Stinchcomb et al., Nature (282) Nov. 1979 pp. 39–43.
Wing, "Development of the molecular biology of the yeast *Yarrowia lipolytica:* I. Development of a transformation system and search for autonomously replicating sequences. II. Cloning and sequencing of the alkaline extracellular protease structural gene.", *Dissertation Abstracts International,* vol. 49, No. 4, pp. 1011-B (1988).
Van der Walt et al, "The yeast genus Yarrowia gen. nov.", *Antonie van Leeuwenhoek,* vol. 46, pp. 517–521 (1980).
Beach et al, "Isolation of chromosomal origins of replication in yeast", *Nature,* vol. 284, pp. 185–187, (1980).

*Primary Examiner*—Richard A. Schwartz
*Assistant Examiner*—James S. Ketter
*Attorney, Agent, or Firm*—Browdy and Neimark

[57] ABSTRACT

The plasmid of the present invention contains Leu 2 gene (β-isopropylmaleate dehydrogenase gene) from *Saccharomycopsis lipolytica* and an autonomously replicating sequence (hereafter referred to as ARS) and can be a shuttle vector between *Escherichia coli* and *Saccharomycopsis lipolytica* since it is produced from shuttle vector pVC 1 of *Escherichia coli* and *Saccharomyces cerevisiae.* An exogenous useful gene is inserted into the plasmid of the present invention, namely, shuttle vector to transform *Escherichia coli,* whereby a large quantity of plasmids are obtained. It becomes possible to produce a useful substance in *Saccharomycopsis lipolytica* as a host using the plasmid.

8 Claims, 3 Drawing Sheets

AUTONOMOUSLY REPLICATING PLASMID AND SACCHAROMYCOPSIS LIPOLYTICA TRANSFORMED THEREWITH

BACKGROUND OF THE INVENTION

The present invention relates to a plasmid containing an autonomously replicating sequence of *Saccharomycopsis lipolytica* and a method for producing the plasmid.

According to the present invention, a plasmid replicatable in cells of *Saccharomycopsis lipolytica* can be produced for the first time.

Application of the plasmid containing an autonomously replicating sequence of *Saccharomycopsis lipolytica* of the present invention has great utility in the field of the fermentation industry.

PRIOR ART

In general, few yeasts contain plasmid therein and it is known that *Saccharomycopsis lipolytica* contains no plasmid at all.

Furthermore, most yeasts do not secrete the enzymes, peptides, etc., produced in the yeast cells but *Saccharomycopsis lipolytica* is exceptionally capable of secreting enzyme, peptide, etc.

PROBLEM TO BE SOLVED BY THE INVENTION

However, any plasmid capable of replicating in cells of *Saccharomycopsis lipolytica* is previously unknown and it was impossible to genetically manipulate production of enzymes, peptides, etc.

MEANS FOR SOLVING THE PROBLEM

As a result of extensive investigations on plasmids capable of replicating in cells of *Saccharomycopsis lipolytica*, the present inventors have succeeded in producing a plasmid capable of replicating in the cells by inserting an autonomously replicating sequence existing on a chromosome of *Saccharomycopsis lipolytica* into a plasmid.

SUMMARY OF THE INVENTION

The present invention relates to a plasmid containing an autonomously replicating sequence of *Saccharomycopsis lipolytica*.

More particularly, the present invention relates to a plasmid containing the Leu 2 gene and an autonomously replicating sequence of *Saccharomycopsis lipolytica*, as well as an ampicillin-resistant gene.

DETAILED DESCRIPTION OF THE INVENTION

Figure 1:
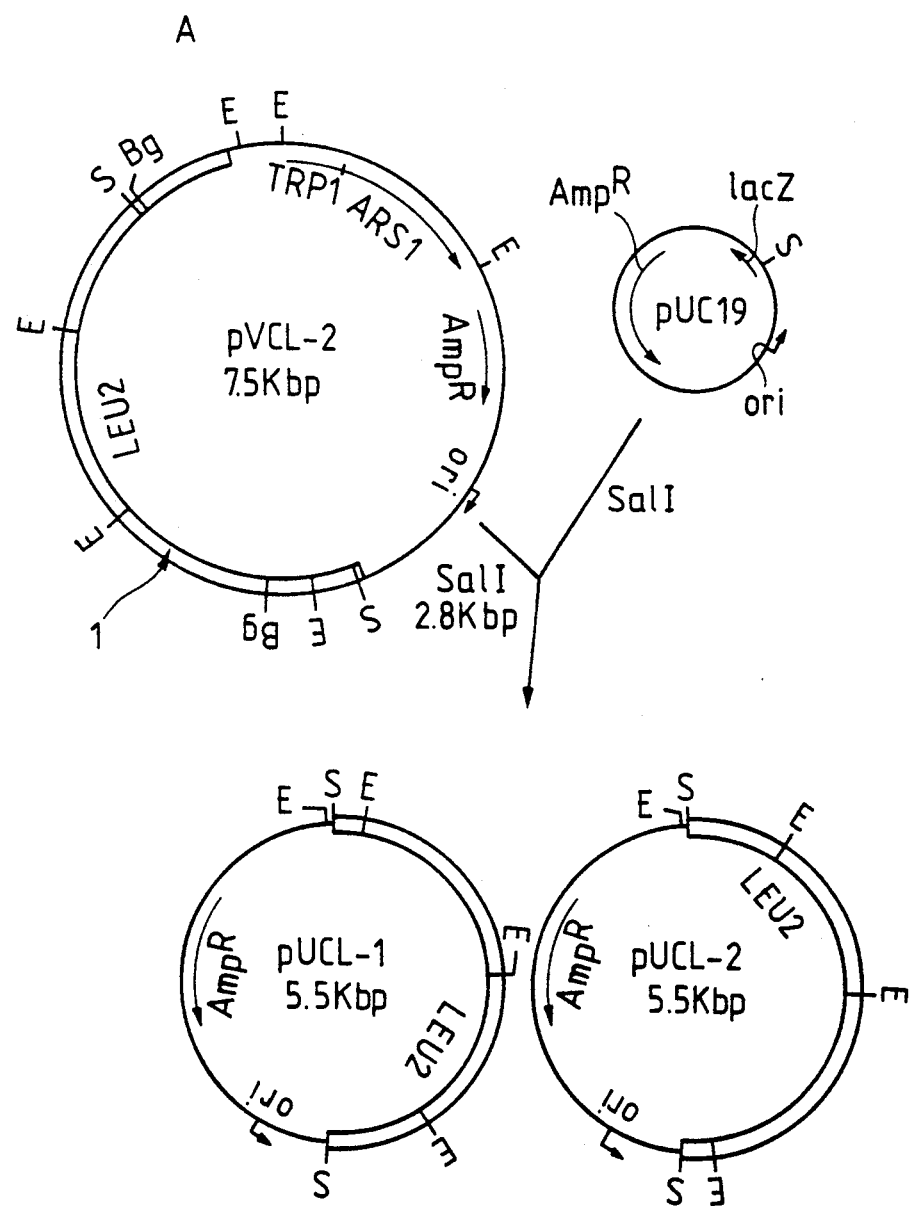
FIG. 1 is a drawing to show production of pUCL-1 and pUCL-2 from pVCL 2 and pUC 19.

The plasmid of the present invention contains the Leu 2 gene ($\beta$-isopropylmaleate dehydrogenase gene) and an autonomously replicating sequence (hereafter referred to as ARS) of *Saccharomycopsis lipolytica* and can be a shuttle vector between *Escherichia coli* and *Saccharomycopsis lipolytica* since it is produced from shuttle vector pVC 1 of *Escherichia coli* and *Saccharomyces cerevisiae*.

An exogenous useful gene is inserted into the plasmid of the present invention, namely, shuttle vector to transform *Escherichia coli*, whereby a large quantity of plasmids are obtained. It becomes possible to produce a useful substance in *Saccharomycopsis lipolytica* as a host using the plasmid.

The novel plasmid of the present invention can be produced, for example, as follows.

Vector pVC 1 of *Saccharomyces cerevisiae* is cleaved with restriction enzyme Bam HI. Fragments obtained by partial cleavage of the whole DNAs of *Saccharomycopsis lipolytica* with restriction enzyme Sau 3AI are inserted at the cleavage site to transform *Escherichia coli*. Ampicillin (Ap)-resistant and $\beta$-galactosidase non-producing transformants are selected and plasmid DNAs are separated from the transformants to make a gene library.

Next, leucine-auxotrophic *Saccharomyces cerevisiae* DKD-5D strain is transformed with plasmid DNAs from the gene library according to the protoplast method of Hinnen et al. (Hinnen, A., Hicks, J. B., Fink, G. R. Proc., Natl. Acad. Sci., 75, 1929 (1978)). Transformants are proliferated in leucine-free minimum medium (composition described below).

| Yeast nitrogen base without amino acid (manufactured by Difco Co., Ltd.) | 0.67% |
|---|---|
| Glucose | 2% |
| Sorbitol | 1.2M |
| Tryptophane | 0.01% |
| Histidine | 0.0035% |
| Agar | 2.0% |

From the obtained transformants, plasmid DNAs are isolated and *Escherichia coli* is transformed with the plasmid DNAs. A colony which is resistant to Ap is selected and novel plasmid pVCL 2 is isolated from the colony.

From this plasmid pVCL 2, plasmids (pUCL-1, pUCL-2, pSL-12 and pSL-13) which are smaller than pVCL 2 and have similar properties and functions are produced.

Next, pSL13 is cleaved with restriction enzyme Bam HI. Fragments obtained by partial cleavage of the whole DNAs of *Saccharomycopsis lipolytica* with restriction enzyme Sau 3AI are inserted at the cleavage site to transform *Escherichia coli*. Ap-resistant and $\beta$-galactosidase non-producing transformants are selected and plasmid DNAs are separated from the transformants to make a gene library.

Leucine-auxotrophic *Saccharomycopsis lipolytica* MX9-11 leu F strain is transformed with the plasmid DNAs from the gene library according to the method of Davidow et al. (Davidow, L. S., Apostolakos, D., O'Donnell, M. M., Proctor, A. R., Ogrydziak, D. M., Wing, R. A., Stasko, I., and DeZeeuw, J. R., Curr. Genet., 10, 39 (1985)). Transformants are proliferated in leucine-free minimum medium (composition described below).

| Yeast nitrogen base without amino acid | 0.67% |
|---|---|
| Glucose | 2% |
| Agar | 2% |

From the obtained transformants, plasmid DNAs are isolated and *Escherichia coli* is transformed by the plasmid DNAs. A colony which is resistant to Ap is selected and novel plasmid pSL13-2 is isolated.

*Escherichia coli* containing plasmid pSL13-2 has been deposited in the Fermentation Research Institute of the Agency of Industrial Science & Technology of Japan under Accession No. pSL13-2 FERM P-9695.

*Saccharomycopsis lipolytica* is transformed with the obtained plasmid pSL13-2; it is confirmed that a number of plasmids are replicated.

Next, the present invention is described in more detail, by referring to the examples.

EXAMPLE 1

(1) Production of Novel Plasmid pVCL 2

After *Saccharomycopsis lipolytica* wild strain (ATCC 44601) was cultured in YEPD medium (composition: 1% yeast extract, 2% peptone and 2% glucose) at 30° C. for 48 hours, the whole DNAs were extracted from the cultured cells and partially cleaved with restriction enzyme Sau 3AI.

On the other hand, shuttle vector pVC 1 (which was produced by ligating fragments of pUC 9 and YRp 7 with restriction enzymes Hae II and Pvu I, respectively; containing Trp 1 of *S. cerevisiae*) of *Escherichia coli* and *Saccharomyces cerevisiae* was cleaved with restriction enzyme Bam HI. Next, both DNAs ligated using T4 DNA ligase and *Escherichia coli* JM 83 strain was then transformed. Transformants were cultured for 12 hours in Ap (50 μg/ml)-containing X-Gal agar medium (upper layer medium (20 ml): 1% Trypton, 0.8% NaCl, 10 mg/l thiamine hydrochloride, 2% agar; lower layer medium (3 ml): 1% Trypton, 0.8% NaCl, 10 mg/l thiamine hydrochloride, 10 μl of 100 mM IPTG (isopropyl β-D-thiogalactopyranoside), 50 μl of 20 mg/ml X-gal (5-bromo-4-chloro-3-indolyl-β-D-galactopyranoside) and 0.6% agar).

Among Ap-resistant colonies formed, 14600 white colonies were obtained. From these colonies, plasmids were isolated and made a gene library of *S. lipolytica*.

Next, leucine-auxotrophic *S. cerevisiae* DKD-5D strain (FERM P-7526) (MATa, trp 1, leu 2, his 3) was transformed with the plasmid DNAs from the gene library described above according to the protoplast transformation method of Hinnen et al. and regeneration was conducted in leucine-deficient agar medium. After culturing at 30° C. for 5 to 7 days, grown colonies were isolated. After culturing in leucine-deficient liquid medium, DNA was isolated from the cells and *Escherichia coli* JA 221 strain was again transformed; colonies which acquired Ap resistance were isolated. Plasmid DNA prepared from the cells was isolated and named pVCL 2.

(2) Preparation of Restriction Enzyme Map of Plasmid pVCL 2

Plasmid pVCL 2 was cleaved with restriction enzymes Bgl II, Eco RI, Kpn I and Sal I. From size of each fragment, a relative position of each cleavage site was determined. The map is shown in FIG. 1A wherein numeral 1 denotes *S. lipolytica*-derived DNA fragment (3.4 kb).

(3) Expression of Plasmid pVCL 2 in *S. cerevisiae* and *S. lipolytica*

Transformation of *S. cerevisiae* with plasmid pVCL 2 according to the lithium metal method of Ito et al. (H. Ito, Y. Fukuda, K. Murata and A. Kimura, J. Bacteriol., 153, 165 (1983)) gave 1500 transformants per 1 μg of DNA.

After plasmid pVCL 2 was cleaved with restriction enzyme Kpn I, *S. lipolytica* MX9-11 leu F strain (leu 2 variant) was transformed according to the method of Davidow et al. (Lance S. Davidow, Diane Apostolakos, Michele M. O'Donnell, Alan R. Proctor, David M. Ogrydziak, Rod A. Wing, Irene Stasko and John R. Dezeeuw, Curr. Genet., 10, 39 (1985)) to give 5915 transformants per 1 μg of DNA.

(4) Production of pUCL-1, pUCL-2, pSL-12 and pSL-13

From plasmid pVCL 2, plasmids (pUCL-1, pUCL-2, pSL-12 and pSL-13) which are smaller than pVCL 2 and have similar properties and functions can be produced. That is, plasmid pVCL 2 was cleaved with restriction enzyme Sal I and a 2.8 kb fraction was isolated. This fraction was inserted into the site obtained by cleaving vector pUC 19 with restriction enzyme Sal I, whereby pUCL-1 and pUCL-2 were prepared (in pUCL-1 and pUCL-2, a direction of inserting the 2.8 kb DNA fragment was reversed).

A map for preparing pUCL-1 and pUCL-2 from pVCL 2 and pUC 19 is shown in FIG. 1.

In FIG. 1, abbreviations for restriction enzymes are as follows.

E: Eco RI, S: Sal I, Bg: Bgl II

Further, pUCL-2 was cleaved with restriction enzymes Bam HI and Bgl II and a 2.7 kb fraction was isolated. This fraction was inserted into the site obtained by cleaving vector pUC 19Bg (the cleavage site of pUC19 with EcoO 109I was converted into the cleavage site with Bgl II) with restriction enzyme Bgl II, whereby pSL-12 and pSL-13 were prepared (in pSL-12 and pSL-13, a direction of inserting the 2.7 kb DNA fragment was reversed).

Figure 2:
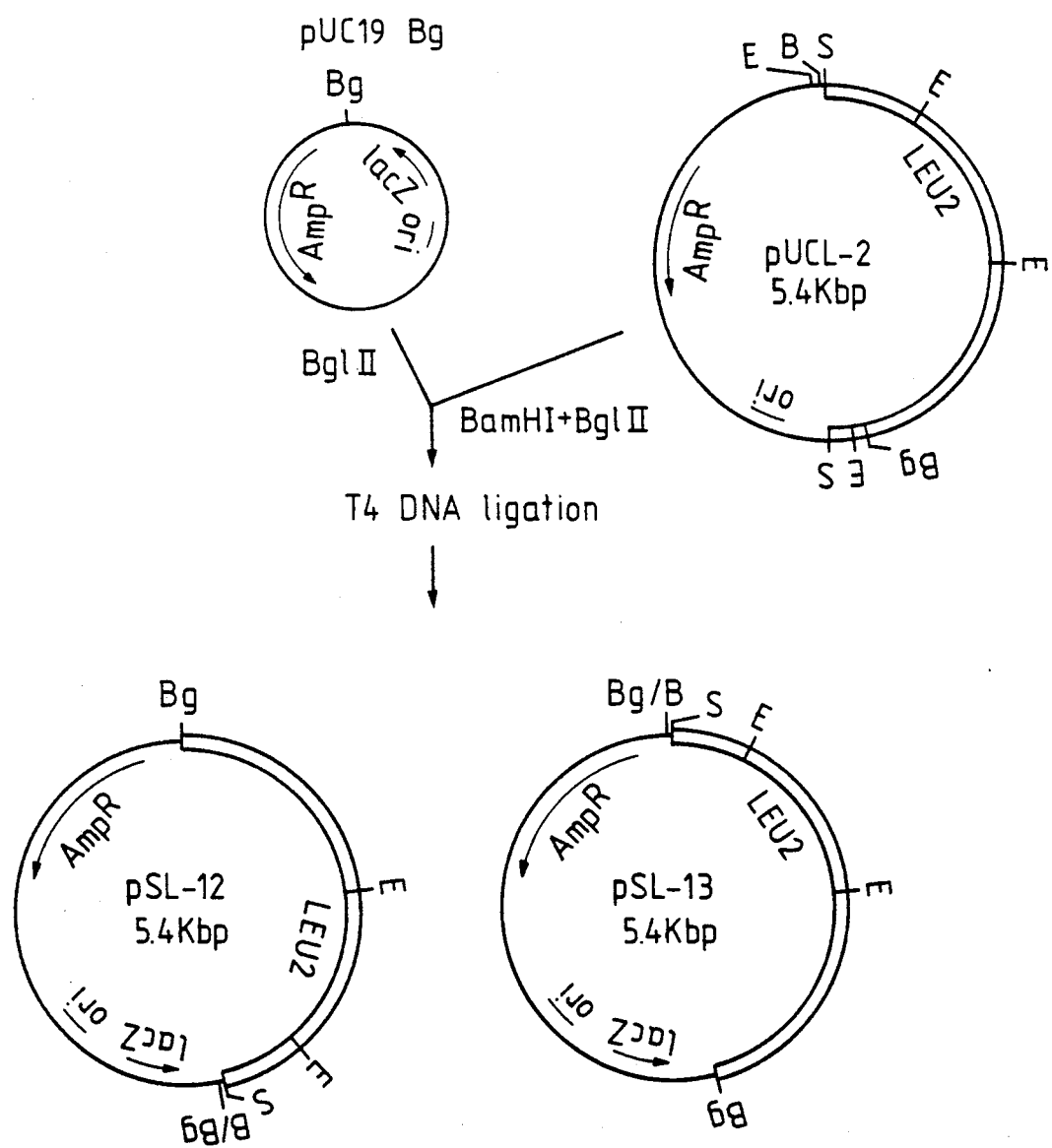
FIG. 2 is a drawing to show production of pSL-12 and pSL-13 from pUC 19Bg and pUCL-2.

A map for preparing pSL-12 and pSL-13 from pUC 19Bg and pUCL-2 is shown in FIG. 2.

In FIG. 2, abbreviations for restriction enzymes are as follows.

B: Bam HI, Bg: Bgl II, S: Sal I, E: Eco RI

(5) Expression of Plasmids pUCL-1 and pSL-13 in *S. lipolytica*

*S. lipolytica* MX9-11 leu F (leu 2 variant) was transformed with plasmids pUCL-1 and pSL-13 according to the method of Davidow et al. The results shown in Table 1 were obtained.

TABLE 1

| Transformation of *S. lipolytica* MX9-11 | | |
| --- | --- | --- |
| Host Strain | Plasmid DNA | Efficiency of Transformation* |
| MX9-11 leu F | pUCL-1 No cleavage | 10 |
| | Cleavage with Bgl II | 4325 |
| | Cleavage with Eco RV | 1785 |
| | Cleavage with Xho I | 1300 |
| | No addition | 0 |
| | pSL-13 No cleavage | 6 |
| | Cleavage with Xho I | 1000 |
| | No addition | 0 |

*The efficiency indicates the number of transformants per 1 μg of DNA.

(6) Production of Novel Plasmid pSL13-2

After culturing *S. lipolytica* wild strain (ATCC 44601) in YEPD medium at 30° C. for 48 hours, the whole DNAs were extracted from the culture and partially cleaved with restriction enzyme Sau 3AI. On the other hand, plasmid pSL-13 was cleaved with restriction enzyme Bam HI. Next, both DNAs were ligated with each other using T4 DNA ligase and *Escherichia coli* JM 109 was then transformed. Transformants were cultured for 12 hours in Ap (50 μg/ml)-containing X-Gal agar medium.

Among Ap-resistant colonies formed, 2500 white colonies were obtained. From these colonies, plasmids were isolated and made a gene library of *S. lipolytica*.

Next, *S. lipolytica* MX9-11 leu F strain (leu 2 variant) was transformed with the plasmid DNAs from the gene library described above according to the Davidow et al. method and regeneration was conducted in leucine-deficient agar medium. After culturing at 30° C. for 4 to 5 days, grown colonies were isolated. After culturing in leucine-deficient liquid medium, DNA was isolated from the cells and *Escherichia coli* JM 109 strain was again transformed and colonies which acquired Ap resistance were isolated. Plasmid DNA prepared from the cells was isolated and named pSL 13-2.

*Escherichia coli* JM 109 containing pSL 13-2 has been deposited in the Fermentation Research Institute of the Agency of Industrial Science & Technology of Japan under Accession No. pSL13-2 FERM P-9695.

(7) Expression of Plasmid pSL13-2 in *S. lipolytica*

Transformation of *S. lipolytica* MX9-11 leu F with non-cleaved plasmid pSL13-2 according to the method of Davidow et al. gave 577 transformants per 1 μg of DNA. Using plasmid pSL 13, transformation was performed under the same conditions but only 0.6 transformant was obtained per 1 μg of DNA. Therefore, it was recognized that pSL13-2 contained ARS functioning in *S. lipolytica*.

(8) Production of Restriction Enzyme Map of Plasmid pSL13-2

Figure 3:
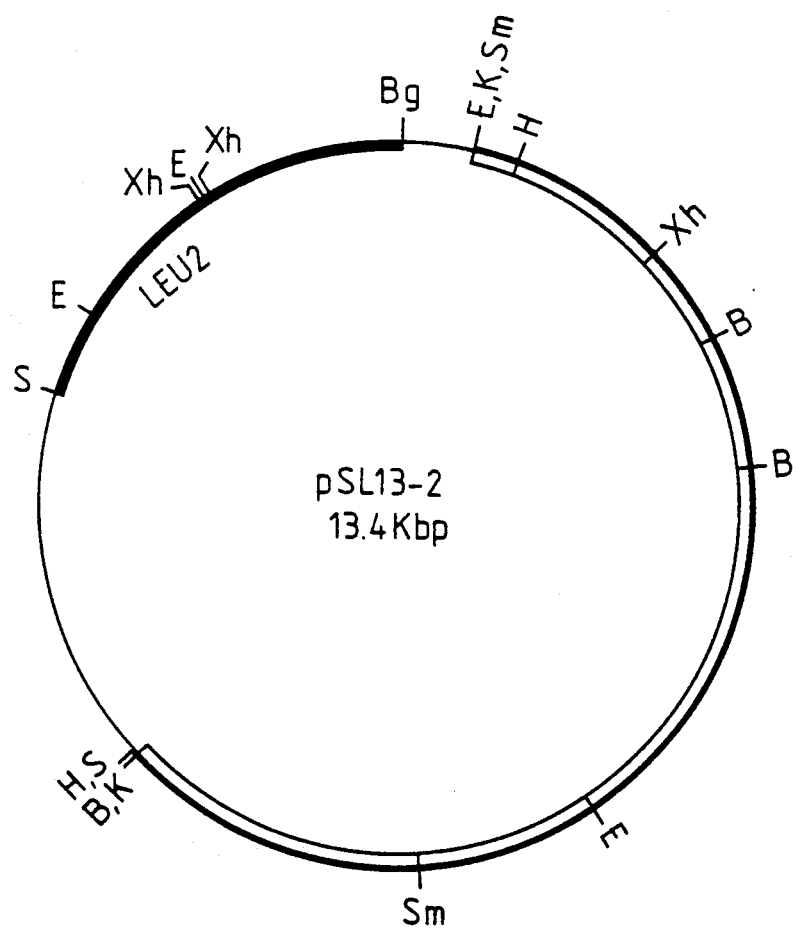
FIG. 3 shows a restriction enzyme map of pSL13-2.

Plasmid pSL13-2 was cleaved with restriction enzymes Bam HI, Eco RI, Kpn I, Hind III, Sma I and Xho I. From size of each fragment, a relative position of each cleavage site was determined, which is shown in FIG. 3. In FIG. 3, abbreviations for restriction enzymes are as follows.

B: Bam HI, Bg: Bgl II, E: Eco RI, K: Kpn I,
H: Hind III, S: Sal I, Sm: Sma I, Xh: Xho I

What is claimed is:

1. A plasmid capable of autonomous replication in *Saccharomycopsis lipolytica*, containing the autonomously replicating sequence existing in the DNA of *Saccharomycopsis lipolytica* and which is present in plasmid pSL13-2 (FERM P-9695).

2. A plasmid in accordance with claim 1, comprising plasmid pSL13-2 (FERM P-9695).

3. A plasmid according to claim 1, wherein said plasmid is a shuttle vector which autonomously replicates in *Escherichia coli*.

4. A plasmid according to claim 3, wherein said plasmid is a shuttle vector which autonomously replicates in *Escherichia coli* and further comprises a gene exogenous to *Saccharomycopsis lipolytica*.

5. A plasmid according to claim 1, wherein said plasmid further comprises a detectable genetic marker and a gene exogenous to *Saccharomycopsis lipolytica*.

6. A plasmid in accordance with claim 5, comprising plasmid pSL13-2 (FERM P-9695).

7. A transformant yeast comprising a *Saccharomycopsis lipolytica* yeast transformed by a plasmid according to claim 5, said plasmid autonomously replicating in said yeast.

8. A transformant yeast according to claim 7 in which the plasmid is pSL13-2 (FERM P-9695).

* * * * *